(12) United States Patent
Nakagawa et al.

(10) Patent No.: US 9,561,213 B2
(45) Date of Patent: Feb. 7, 2017

(54) CANDESARTAN CILEXETIL-CONTAINING PREPARATION

(71) Applicant: SAWAI PHARMACEUTICAL CO., LTD., Osaka (JP)

(72) Inventors: Tomoya Nakagawa, Osaka (JP); Yasushi Fukuhara, Osaka (JP); Kenji Uetsuki, Osaka (JP); Masaya Hizaki, Osaka (JP)

(73) Assignee: SAWAI PHARMACEUTICAL CO., LTD, Osaka (JP)

( * ) Notice: Subject to any disclaimer, the term of this patent is extended or adjusted under 35 U.S.C. 154(b) by 0 days.

(21) Appl. No.: 14/728,990

(22) Filed: Jun. 2, 2015

(65) Prior Publication Data

US 2015/0265579 A1   Sep. 24, 2015

Related U.S. Application Data

(63) Continuation of application No. PCT/JP2013/083279, filed on Dec. 5, 2013.

(30) Foreign Application Priority Data

Dec. 5, 2012 (JP) .................. 2012-265916

(51) Int. Cl.
- *A61K 31/4184* (2006.01)
- *A61K 47/10* (2006.01)
- *A61K 9/20* (2006.01)

(52) U.S. Cl.
CPC ......... *A61K 31/4184* (2013.01); *A61K 9/2013* (2013.01); *A61K 47/10* (2013.01)

(58) Field of Classification Search
CPC ............................ A61K 31/4184; A61K 47/10
See application file for complete search history.

(56) References Cited

FOREIGN PATENT DOCUMENTS

| EP | 0 546 358 A2 | * | 6/1993 |
|---|---|---|---|
| EP | 2952187 A1 | | 12/2015 |
| JP | H05-194218 A | | 8/1993 |
| JP | 2008-528456 A | | 7/2008 |
| JP | 2009-107944 A | | 5/2009 |
| JP | 2010-522692 A | | 7/2010 |
| JP | 2010-535212 A | | 11/2010 |
| JP | 2012-051829 A | | 3/2012 |
| JP | 2012-149056 A | | 8/2012 |
| JP | 2012-153629 A | | 8/2012 |
| JP | 2012-162467 A | | 8/2012 |
| JP | 2013-224265 A | | 10/2013 |
| WO | 2006/079496 A1 | | 8/2006 |
| WO | 2006/113631 A2 | | 10/2006 |
| WO | 2008/123536 A1 | | 10/2008 |
| WO | 2009/017812 A3 | | 2/2009 |

OTHER PUBLICATIONS

International Search Report mailed on Feb. 10, 2014 regarding International Patent Application No. PCT/JP2013/083279.
Written Opinion mailed on Feb. 10, 2014 regarding International Patent Application No. PCT/JP2013/083279.
Extended European search report for the counter European Patent application No. 13860117.4 issued on Jun. 29, 2016.

\* cited by examiner

*Primary Examiner* — James D Anderson
(74) *Attorney, Agent, or Firm* — Typha IP LLC

(57) ABSTRACT

A candesartan cilexetil-containing preparation contains candesartan cilexetil and lauromacrogol. The lauromacrogol may be contained at a ratio of 2.4 parts by weight or less with respect to 100 parts by weight of the candesartan cilexetil-containing preparation. The candesartan cilexetil-containing preparation may further contain at least one kind of pharmacologically acceptable additives among a diluent, a disintegrant and a binder.

5 Claims, 3 Drawing Sheets

FIG. 3

|  | Example 9 | Example 10 | Example 11 | Example 12 | Example 13 | Example 14 |
|---|---|---|---|---|---|---|
| Amount of Lauromacrogol (Parts by Wight) | 2.40 | 1.60 | 0.80 | 0.40 | 0.16 | 0.08 |
| INITIAL (kg) | 2.7 | 3.1 | 3.5 | 5.4 | 7.3 | 6.7 |
| 25°C, 75% 1W (kg) | 1.9 | 2.1 | 2.4 | 3.4 | 5.4 | 3.7 |
| 40°C, 75% 1W (kg) | 1.3 | 1.6 | 2.0 | 3.7 | 5.3 | 4.8 |

FIG. 4

|  | Example 9 | Example 10 | Example 11 | Example 12 | Example 13 | Example 14 |
|---|---|---|---|---|---|---|
| Amount of Lauromacrogol (Parts by Wight) | 2.40 | 1.60 | 0.80 | 0.40 | 0.16 | 0.08 |
| INITIAL (%) | 78.4 - 85.4 | 77.3 - 87.0 | — | 82.3 - 85.6 | 89.4 - 90.6 | 94.2 - 97.0 |

CANDESARTAN CILEXETIL-CONTAINING PREPARATION

CROSS REFERENCE TO RELATED APPLICATIONS

This application is based upon and claims the benefit of priority from the prior Japanese Patent Application No. 2012-265916, filed on Dec. 5, 2012 and PCT Application No. PCT/JP2013/083279, filed on Dec. 5, 2013, the entire contents of which are incorporated herein by reference.

FIELD

The present invention relates to a candesartan cilexetil-containing preparation, and specifically to a stable candesartan cilexetil-containing preparation in which generation of related substances is inhibited during a production process or storage thereof.

BACKGROUND

Candesartan cilexetil, which is an angiotensin II receptor antagonist, is widely used as a therapeutic drug for hypertension. Regarding candesartan cilexetil, it is known that the crystals thereof are distorted by pressure, friction, heat or the like during granulation, tableting or the like in formulation process thereof, and as a result, the purity is decreased and over-time generation of related substances occurs. So far, various methods have been proposed for stabilizing candesartan cilexetil preparations. For example, Japanese Laid-Open Patent Publication No. Hei 5-194218 describes that in order to stabilize a candesartan cilexetil preparation, a low-melting fatty oil-like substance is incorporated to inhibit the generation of related substances. Japanese PCT National Phase Laid-Open Patent Publication No. 2008-528456 describes that a hydrophilic substance with hydrocolloidal properties is incorporated to adequately stabilize the candesartan cilexetil, against its degradation during the tableting process.

Japanese PCT National Phase Laid-Open Patent Publication No. 2010-522692 describes incorporating a pH adjuster to stabilize a candesartan cilexetil compound in the preparation. Japanese PCT National Phase Laid-Open Patent Publication No. 2010-535212 describes incorporating at least one kind of nonionic surfactants at a ratio of about 0.01 to 10% by weight with respect to the pharmaceutical composition. Japanese Laid-Open Patent Publication No. 2012-51829 describes incorporating sodium stearyl fumarate. Japanese Laid-Open Patent Publication No. 2012-149056 describes incorporating triethyl citrate. Japanese Laid-Open Patent Publication No. 2012-153629 describes incorporating stearic acid. Japanese Laid-Open Patent Publication No. 2012-162467 describes incorporating D-mannitol to perform fluidized-bed granulation.

SUMMARY

As described above, a method for improving the stability of the candesartan cilexetil in a preparation is desired.

The present invention solves the above-described problems by means of a different method from methods reported so far. An object of the present invention is to provide a stable candesartan cilexetil-containing preparation in which generation of related substances is inhibited during a production process or storage thereof.

According to an embodiment of the present invention, a candesartan cilexetil-containing preparation containing candesartan cilexetil and lauromacrogol is provided.

The lauromacrogol may be contained at a ratio of 2.4 parts by weight or less with respect to 100 parts by weight of the candesartan cilexetil-containing preparation.

The lauromacrogol may be selected from polyoxyethylene(2) lauryl ether, polyoxyethylene(4.2) lauryl ether, polyoxyethylene(9) lauryl ether, polyoxyethylene(21) lauryl ether, and polyoxyethylene(25) lauryl ether.

The lauromacrogol may be polyoxyethylene(25) lauryl ether.

The candesartan cilexetil-containing preparation may further contain at least one kind of pharmacologically acceptable additives among a diluent, a disintegrant and a binder.

The additive may be contained in the range of 500 parts by weight or greater and 10000 parts by weight or less with respect to 100 parts by weight of candesartan cilexetil.

BRIEF DESCRIPTION OF DRAWINGS

FIG. 3 shows results of hardness measurement on candesartan cilexetil-containing compositions in examples of the present invention; and FIG. 4 shows results of dissolution measurement on candesartan cilexetil from the candesartan cilexetil-containing compositions in examples of the present invention.

DESCRIPTION OF EMBODIMENTS

Figure 1:
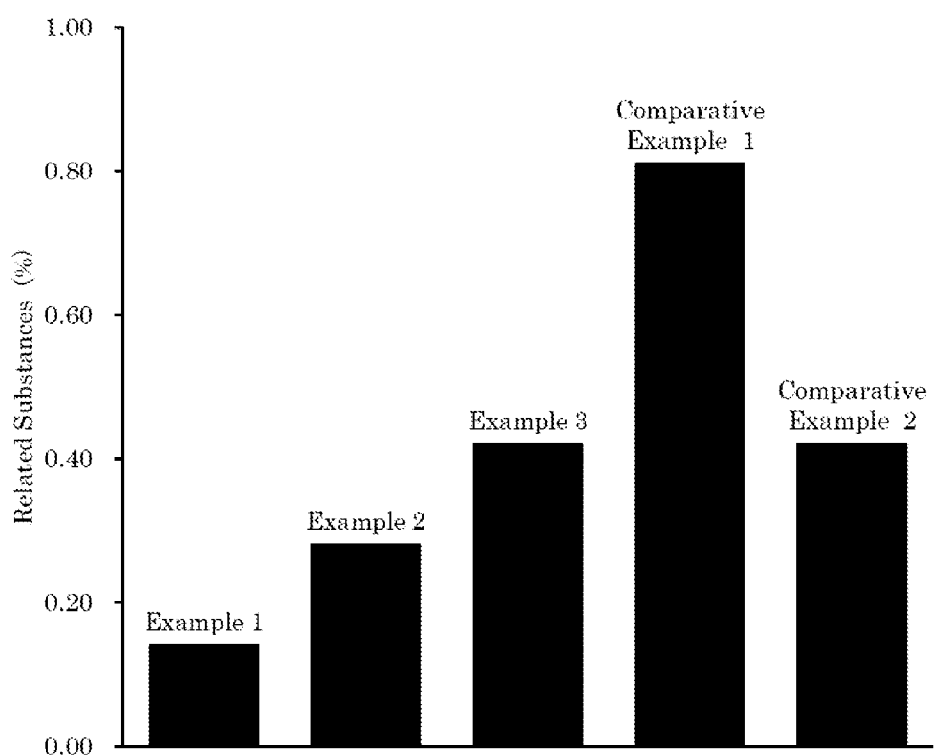
FIG. 1 shows results of purity measurement on candesartan cilexetil-containing compositions in examples and comparative examples of the present invention.

The present inventors made a research on an additive capable of inhibiting generation of related substances in a candesartan cilexetil-containing preparation. As a result of the research, the present inventors found that generation of related substances in a candesartan cilexetil-containing preparation could be inhibited during the preparation process or storage thereof by incorporating lauromacrogol thereto, and thus completed the present invention. The present invention reports that lauromacrogol contributes to stabilization of candesartan cilexetil in a tablet for the first time in history.

Hereinafter, a candesartan cilexetil-containing preparation according to the present invention will be described with reference to the drawings. The candesartan cilexetil-containing preparation according to the present invention is not limited to any of the following embodiments and examples.

A candesartan cilexetil-containing preparation according to the present invention contains lauromacrogol. Specifically, lauromacrogol is contained at a ratio of 0.01 parts by weight or greater and 2.4 parts by weight or less with respect to 100 parts by weight of the candesartan cilexetil-containing preparation.

In an embodiment according to the present invention, it is not preferable that lauromacrogol is contained at a ratio greater than 2.4 parts by weight with respect to 100 parts by weight of the candesartan cilexetil-containing preparation. When lauromacrogol is contained at a ratio greater than 2.4 parts by weight, the hardness of the tablet is decreased and the dissolution of candesartan cilexetil is decreased.

Candesartan cilexetil is an active ingredient of a candesartan cilexetil-containing preparation according to the present invention, and has a chemical name of (RS)-1-[(cyclohexyloxy)carbonyloxy]ethyl 2-ethoxy-1-{[2'-(1H-tetrazole-5-yl)-biphenyl-4-yl]methyl}-1H-benzimidazole-7-carboxylate.

Lauromacrogol, which is contained in a candesartan cilexetil-containing preparation according to the present invention is polyoxyethylene lauryl ether. Usable examples of the polyoxyethylene lauryl ether are polyoxyethylene(2) lauryl ether, polyoxyethylene(4.2) lauryl ether, polyoxyethylene(9) lauryl ether, polyoxyethylene(21) lauryl ether, and polyoxyethylene(25) lauryl ether. Among these, polyoxyethylene(21) lauryl ether and polyoxyethylene(25) lauryl ether are preferable. Especially, polyoxyethylene(25) lauryl ether (produced by Nikko Chemicals Co., Ltd.; trade name: BL-25) is preferably usable in a candesartan cilexetil-containing preparation according to the present invention.

A candesartan cilexetil-containing preparation according to the present invention may contain at least one kind of pharmacologically acceptable additives among commonly used diluents, disintegrants and binders.

Usable diluents include, for example, crystalline cellulose, starches such as corn starch, lactose, powdered sugar, granulated sugar, glucose, mannitol, light anhydrous silicic acid, talc, magnesium oxide, magnesium carbonate, calcium carbonate, anhydrous dibasic calcium phosphate, tribasic calcium phosphate, xylitol, sorbitol, and the like. These diluents may be used independently or in a combination of two or more.

Usable disintegrants include, for example, crystalline cellulose, sodium carboxymethyl starch, carmellose, carmellose calcium, carmellose sodium, croscarmellose sodium, crosslinked polyvinylpyrrolidone, low substituted hydroxypropylcellulose, starches and the like. These disintegrants may be used independently or in a combination of two or more.

Usable binders are pharmacologically acceptable binders including, for example, sucrose, gelatin, powdered acacia, methylcellulose, hydroxypropylmethylcellulose, hydroxypropylcellulose, carboxymethylcellulose (carmellose), crystalline cellulose-carboxymethylcellulose sodium, polyvinylpyrrolidone, pullulan, dextrin, tragacanth, sodium alginate, pregelatinized starch, polyvinyl alcohol and the like. These binders may be used independently or in a combination of two or more.

An additive which is at least one kind among these diluents, disintegrants and binders is contained preferably in the range of 500 parts by weight or greater and 10000 parts by weight or less, more preferably in the range of 700 parts by weight or greater and 8000 parts by weight or less, and still more preferably in the range of 900 parts by weight or greater and 7000 parts by weight or less, with respect to 100 parts by weight of candesartan cilexetil.

Candesartan cilexetil may be combined with, in addition to a pharmacologically acceptable additive such as a diluent, a disintegrant, a binder or the like, any of other commonly used pharmacologically acceptable additives including, for example, lubricants, fluidizer, antistatic agents, surfactants, flavoring agents, wetting agents, fillers, bulking agents, adsorbents, preservatives (e.g., antiseptics), buffers, disintegration extenders, colorants and the like.

Usable lubricants include, for example, magnesium stearate, light anhydrous silicic acid, talc, calcium stearate, sodium stearyl fumarate, sucrose esters of fatty acid, L-leucine, and the like. Usable antistatic agents include, for example, light anhydrous silicic acid and the like. Usable surfactants include, for example, anionic surfactants such as sodium alkylsulfate; nonionic surfactants such as polyoxyethylene sorbitan fatty acid ester, polyoxyethylene fatty acid ester, polyoxyethylene castor oil derivative; and the like. Usable flavoring agents include, for example, fragrances; sweetening agents such as sucrose, lactose, mannitol, xylitol, saccharin, saccharin sodium, aspartame, stevioside, sucralose, acesulfame potassium, thaumatin, erythritol; and the like. Usable wetting agents include, for example, polyethylene glycol (macrogol), glycerin, propylene glycol, and the like. These commonly used additives other than the diluents, disintegrants and binders may also be used independently or in a combination of two or more.

According to the present invention, a stable candesartan cilexetil-containing preparation in which generation of related substances is inhibited during a production process or storage thereof can be obtained by incorporation of lauromacrogol.

(Production Method)

A candesartan cilexetil-containing preparation according to the present invention can be produced by a method known in the pharmaceutical field. For example, tablet can be produced by performing respective operations such as mixing, granulation, drying, particle size regulation, and tableting with respect to candesartan cilexetil, lauromacrogol, an additive such as a diluent, a disintegrant, a binder or the like using commonly used solvent according to a method well known in the art. Between the particle size regulation and the tableting, a disintegrant, a lubricant or the like may be mixed. Among these operations, granulation may be performed by use of an apparatus such as, for example, an agitation granulator, a fluidized-bed granulator, a biaxial granulator or the like. Tableting may be performed by use of a commercially available tableting machine.

In this embodiment, lauromacrogol is incorporated at a ratio of 2.4 parts by weight or less with respect to 100 parts by weight of the candesartan cilexetil-containing preparation. Preferably, lauromacrogol is incorporated at a ratio of 0.01 parts by weight or greater and 2.4 parts by weight or less with respect to 100 parts by weight of the candesartan cilexetil-containing preparation.

In this embodiment, uncoated tablets or post-granulation uncoated granules may be coated. Coating is preferably performed by use of a film coating machine, a fluidized-bed granulator or the like. Coating can be performed with a coating agent well known in the art. Usable coating agents include, for example, hydroxypropylmethylcellulose, hydroxypropylcellulose, methylcellulose, polyvinyl alcohol, polyvinylpyrrolidone, polyethylene glycol, hydroxypropylmethylcellulose acetate succinate, hydroxypropylmethylcellulose phthalate, cellulose acetate phthalate, aminoalkyl methacrylate copolymer E, aminoalkyl methacrylate copolymer RS, methacrylic acid copolymer L, methacrylic acid copolymer LD, methacrylic acid copolymer S, dried methacrylic acid copolymer LD, ethyl acrylate-methyl methacrylate copolymer dispersion, sucrose and the like.

According to a method for producing a candesartan cilexetil-containing preparation in this embodiment, lauromacrogol is incorporated. Thus, a candesartan cilexetil-containing preparation in which generation of related substances is inhibited during a production process or storage thereof can be produced.

EXAMPLES

The above-described candesartan cilexetil-containing preparation according to the present invention will be described in more detail by way of specific production methods and test results thereof.

Example 1

After mixing 10.0 g of candesartan cilexetil, 464 g of lactose hydrate, and 100 g of corn starch by use of a fluidized-bed granulator (produced by Powrex Corporation), an aqueous solution containing 25 g of hydroxypropylcellulose and 0.25 g of lauromacrogol (produced by Nikko Chemicals Co., Ltd.; trade name: BL-25) was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.6 mm. Thus, the tablets were obtained.

Example 2

After mixing 10.0 g of candesartan cilexetil, 464 g of lactose hydrate, and 100 g of corn starch by use of a fluidized-bed granulator (produced by Powrex Corporation), an aqueous solution containing 25 g of hydroxypropylcellulose and 0.10 g of lauromacrogol (produced by Nikko Chemicals Co., Ltd.; trade name: BL-25) was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.6 mm (at the same tableting pressure as that in Example 1). Thus, the tablets were obtained.

Example 3

After mixing 10.0 g of candesartan cilexetil, 464 g of lactose hydrate, and 100 g of corn starch by use of a fluidized-bed granulator (produced by Powrex Corporation), an aqueous solution containing 25 g of hydroxypropylcellulose and 0.05 g of lauromacrogol (produced by Nikko Chemicals Co., Ltd.; trade name: BL-25) was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.6 mm (at the same tableting pressure as that in Example 1). Thus, the tablets were obtained.

Example 4

After mixing 10.0 g of candesartan cilexetil, 463 g of lactose hydrate, and 100 g of corn starch by use of a fluidized-bed granulator (produced by Powrex Corporation), an aqueous solution containing 25 g of hydroxypropylcellulose and 1.00 g of lauromacrogol (produced by Nikko Chemicals Co., Ltd.; trade name: BL-25) was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.5 mm (at a tableting pressure higher than that in Examples 1 through 3). Thus, the tablets were obtained.

Example 5

After mixing 10.0 g of candesartan cilexetil, 463.5 g of lactose hydrate, and 100 g of corn starch by use of a fluidized-bed granulator (produced by Powrex Corporation), an aqueous solution containing 25 g of hydroxypropylcellulose and 0.50 g of lauromacrogol (produced by Nikko Chemicals Co., Ltd.; trade name: BL-25) was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.5 mm (at the same tableting pressure as that in Example 4). Thus, the tablets were obtained.

Example 6

After mixing 10.0 g of candesartan cilexetil, 464 g of lactose hydrate, and 100 g of corn starch by use of a fluidized-bed granulator (produced by Powrex Corporation), an aqueous solution containing 25 g of hydroxypropylcellulose and 0.25 g of lauromacrogol (produced by Nikko Chemicals Co., Ltd.; trade name: BL-25) was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.5 mm (at the same tableting pressure as that in Example 4). Thus, the tablets were obtained.

Example 7

After mixing 10.0 g of candesartan cilexetil, 464 g of lactose hydrate, and 100 g of corn starch by use of a fluidized-bed granulator (produced by Powrex Corporation), an aqueous solution containing 25 g of hydroxypropylcellulose and 0.10 g of lauromacrogol (produced by Nikko Chemicals Co., Ltd.; trade name: BL-25) was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.5 mm (at the same tableting pressure as that in Example 4). Thus, the tablets were obtained.

Example 8

After mixing 10.0 g of candesartan cilexetil, 464 g of lactose hydrate, and 100 g of corn starch by use of a fluidized-bed granulator (produced by Powrex Corporation), an aqueous solution containing 25 g of hydroxypropylcellulose and 0.05 g of lauromacrogol (produced by Nikko Chemicals Co., Ltd.; trade name: BL-25) was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.5 mm (at the same tableting pressure as that in Example 4). Thus, the tablets were obtained.

Example 9

After mixing 60.0 g of candesartan cilexetil, 399 g of lactose hydrate, and 100 g of corn starch by use of a fluidized-bed granulator (produced by Powrex Corporation), an aqueous solution containing 25 g of hydroxypropylcellulose, 15.0 g of lauromacrogol (produced by Nikko Chemicals Co., Ltd.; trade name: BL-25) and 0.15 g of food yellow No. 5 was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.5 mm (at the same tableting pressure as that in Example 4). Thus, the tablets were obtained.

Example 10

After mixing 60.0 g of candesartan cilexetil, 404 g of lactose hydrate, and 100 g of corn starch by use of a fluidized-bed granulator (produced by Powrex Corporation), an aqueous solution containing 25 g of hydroxypropylcellulose, 10.0 g of lauromacrogol (produced by Nikko Chemicals Co., Ltd.; trade name: BL-25) and 0.15 g of food yellow No. 5 was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.5 mm (at the same tableting pressure as that in Example 4). Thus, the tablets were obtained.

Example 11

After mixing 60.0 g of candesartan cilexetil, 409 g of lactose hydrate, and 100 g of corn starch by use of a fluidized-bed granulator (produced by Powrex Corporation), an aqueous solution containing 25 g of hydroxypropylcellulose, 5.00 g of lauromacrogol (produced by Nikko Chemicals Co., Ltd.; trade name: BL-25) and 0.15 g of food yellow No. 5 was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.5 mm (at the same tableting pressure as that in Example 4). Thus, the tablets were obtained.

Example 12

After mixing 60.0 g of candesartan cilexetil, 411.5 g of lactose hydrate, and 100 g of corn starch by use of a fluidized-bed granulator (produced by Powrex Corporation), an aqueous solution containing 25 g of hydroxypropylcellulose, 2.50 g of lauromacrogol (produced by Nikko Chemicals Co., Ltd.; trade name: BL-25) and 0.15 g of food yellow No. 5 was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.5 mm (at the same tableting pressure as that in Example 4). Thus, the tablets were obtained.

Example 13

After mixing 60.0 g of candesartan cilexetil, 413 g of lactose hydrate, and 100 g of corn starch by use of a fluidized-bed granulator (produced by Powrex Corporation), an aqueous solution containing 25 g of hydroxypropylcellulose, 1.00 g of lauromacrogol (produced by Nikko Chemicals Co., Ltd.; trade name: BL-25) and 0.15 g of food yellow No. 5 was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.5 mm (at the same tableting pressure as that in Example 4). Thus, the tablets were obtained.

Example 14

After mixing 60.0 g of candesartan cilexetil, 413.5 g of lactose hydrate, and 100 g of corn starch by use of a fluidized-bed granulator (produced by Powrex Corporation), an aqueous solution containing 25 g of hydroxypropylcellulose, 0.50 g of lauromacrogol (produced by Nikko Chemicals Co., Ltd.; trade name: BL-25) and 0.15 g of food yellow No. 5 was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.5 mm (at the same tableting pressure as that in Example 4). Thus, the tablets were obtained.

Comparative Example 1

After mixing 10.0 g of candesartan cilexetil, 464 g of lactose hydrate, and 100 g of corn starch by use of a fluidized-bed granulator (produced by Powrex Corporation), an aqueous solution containing 25 g of hydroxypropylcellulose was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.6 mm (at the same tableting pressure as that in Example 1). Thus, the tablets were obtained.

Comparative Example 2

After mixing 12.0 g of candesartan cilexetil, 483.6 g of lactose hydrate, 120 g of corn starch, and 48.0 g of stearic acid by use of a fluidized-bed granulator (produced by Powrex Corporation), an aqueous solution containing 30 g of hydroxypropylcellulose was sprayed thereto, and granulation and drying were performed. The particle size of resultant granules was regulated through a No. 22 sieve. The obtained particle-size regulated granules, 24.0 g of carmellose calcium, and 2.40 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 120.0 mg and a thickness of 2.5 mm (at the same tableting pressure as that in Example 1). Thus, the tablets were obtained.

Comparative Example 3

After mixing 10.0 g of candesartan cilexetil, 464 g of lactose hydrate, and 100 g of corn starch by use of a fluidized-bed granulator (produced by Powrex Corporation), an aqueous solution containing 25 g of hydroxypropylcellulose was sprayed thereto, and granulation and drying were performed. The particle size of resultant granules was regulated through a No. 22 sieve. The obtained particle-size regulated granules, 20.0 g of croscarmellose sodium, and 6.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 125.0 mg and a thickness of 2.5 mm (at the same tableting pressure as that in Example 4). Thus, the tablets were obtained.

Comparative Example 4

After mixing 10.0 g of candesartan cilexetil, 477 g of lactose hydrate, and 100 g of corn starch by use of a fluidized-bed granulator (produced by Powrex Corporation), an aqueous solution containing 20 g of hydroxypropylcellulose and 13.0 g of macrogol 6000 was sprayed thereto, and granulation and drying were performed. The particle size of resultant granules was regulated through a No. 22 sieve. The obtained particle-size regulated granules, 28.0 g of carmellose calcium, and 2.00 g of magnesium stearate were mixed by a V blender (produced by Fuji Paudal Co., Ltd.). The resultant mixture was tableted by a rotary tableting machine (produced by Kikusui Seisakusho Ltd.) such that the tablets would each have a weight of 130.0 mg and a thickness of 2.6 mm (at the same tableting pressure as that in Example 4). Thus, the tablets were obtained.

(Purity)

On the tablets in Examples 1 through 8 and Comparative examples 1 through 4, the purity was evaluated. The purity evaluation was performed as follows. The tablets were stored at 40° C. at 75% RH for 2 weeks, and then a test was performed in conformity to the candesartan cilexetil tablet purity test described in the Japanese Pharmacopoeia Sixteenth Edition. Thus, the purity was measured. The measurement results are shown in FIG. 1 and FIG. 2.

Figure 2:
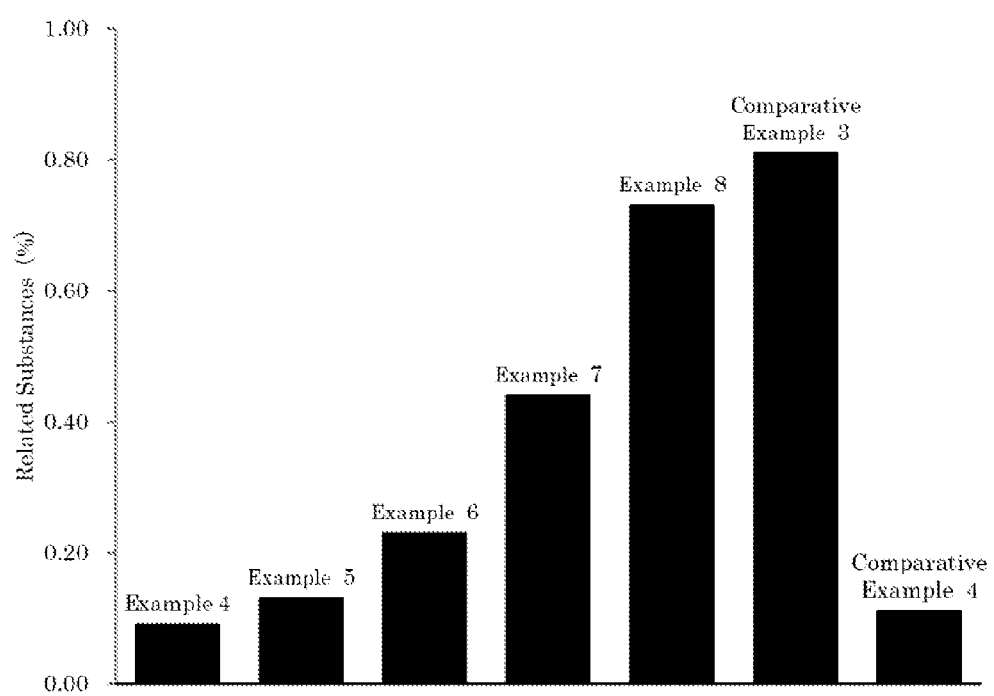
FIG. 2 shows results of purity measurement on candesartan cilexetil-containing compositions in examples and comparative examples of the present invention.

As can be seen from the results shown in FIG. 1 and FIG. 2, a smaller amount of related substances is detected in Examples 1 through 8 than in Comparative examples 1 and 3, in which lauromacrogol is not incorporated. It is also seen regarding Examples 1 through 8 that when the amount of lauromacrogol is larger, the detected amount of related substances is smaller. A low-melting fatty oil-like substance, such as macrogol 6000, is incorporated to inhibit the generation of related substances in the conventional art, as is described in Japanese Laid-Open Patent Publication No. Hei 5-194218. Japanese Laid-Open Patent Publication No. Hei 5-194218 describes that in order to inhibit the generation of related substances, macrogol 6000 is incorporated at a ratio of 5 parts by weight with respect to 100 parts by weight of the candesartan cilexetil-containing preparation in the example. Japanese Laid-Open Patent Publication No. 2012-153629 describes that in order to inhibit the generation of related substances, stearic acid is incorporated at a ratio of 3.1 parts by weight or 6.2 parts by weight with respect to 100 parts by weight of the candesartan cilexetil-containing preparation in the example. In Comparative example 2, stearic acid as stabilizing agent in the conventional art is incorporated. In Comparative example 4, macrogol is incorporated. In these comparative examples, the detected amount of related substances is smaller than in Comparative examples 1 and 3 with no incorporation of stabilizing agent. However, stearic acid should be incorporated at a ratio of 6.7 parts by weight with respect to 100 parts by weight of the candesartan cilexetil-containing preparation to inhibit the generation of related substances at the same level as Example 3, as is shown in Comparative example 2. In Comparative example 4, macrogol 6000 should be incorporated at a ratio of 2.0 parts by weight with respect to 100 parts by weight of the candesartan cilexetil-containing preparation to inhibit the generation of related substances at the same level as Example 4 or 5 in which lauromacrogol is contained at a ratio of 0.16 parts by weight or less with respect to 100 parts by weight of the candesartan cilexetil-containing preparation. Stearic acid or macrogol needs to be incorporated in a larger amount than in Examples 1 through 8 in which lauromacrogol is incorporated. From these results, it is understood that the candesartan cilexetil-containing preparations in Examples 1 through 8, owing to containing lauromacrogol, can significantly inhibit generation of related substances with a smaller amount of the stabilizing agent than in the conventional art.

(Hardness)

Next, on the tablets in Examples 9 through 14, the relationship between the amount of lauromacrogol and the hardness of the tablets was examined. The hardness was measured as follows. The hardness of three tablets in each example was measured by a Schleuniger tablet hardness tester (MODEL 6D), and the average value thereof was set as the hardness of the tablets in the corresponding example. For measuring the hardness of tablets with a score therein, all such tablets were each set such that the surface with the score was directed upward and thus the score was perpendicular to the direction in which the hardness tester would push the tablet. The results of the hardness measurement on the tablets in Examples 9 through 14 are shown in FIG. 3. In addition, the amounts of lauromacrogol of the Examples with respect to 100 parts by weight of the candesartan cilexetil-containing preparation are shown in FIG. 3.

As is clear from FIG. 3, regarding Examples 9 through 14, when the amount of lauromacrogol is larger, the hardness of the tablet is lower.

(Dissolution)

On the tablets in Examples 9 through 14, the relationship between the amount of lauromacrogol and the dissolution of candesartan cilexetil was examined. The dissolution of candesartan cilexetil was measured as follows. A test was performed in conformity to the description on the dissolution of candesartan cilexetil tablet in the Japanese Pharmacopoeia Sixteenth Edition, and the dissolution rate (%) in 45 minutes of candesartan cilexetil was measured. The results of the dissolution measurement of candesartan cilexetil on the tablets in Examples 9 through 14 are shown in FIG. 4. In addition, the amounts of lauromacrogol of the Examples with respect to 100 parts by weight of the candesartan cilexetil-containing preparation are shown in FIG. 4.

As is clear from FIG. 4, regarding Examples 9 through 14, when the amount of lauromacrogol is larger, the dissolution of candesartan cilexetil from the tablet is lower.

The present invention provides a stable candesartan cilexetil-containing preparation in which generation of related substances is inhibited during a production process or storage thereof.

The invention claimed is:

1. A candesartan cilexetil-containing preparation, comprising candesartan cilexetil and lauromacrogol,
   wherein the lauromacrogol is contained at a ratio of 0.16 parts by weight or less with respect to 100 parts by weight of the candesartan cilexetil-containing preparation.

2. The candesartan cilexetil-containing preparation according to claim 1, wherein the lauromacrogol is selected from polyoxyethylene(2) lauryl ether, polyoxyethylene(4.2) lauryl ether, polyoxyethylene(9) lauryl ether, polyoxyethylene(21) lauryl ether, and polyoxyethylene(25) lauryl ether.

3. The candesartan cilexetil-containing preparation according to claim 1, wherein the lauromacrogol is polyoxyethylene(25) lauryl ether.

4. The candesartan cilexetil-containing preparation according to claim 1, further comprising at least one kind of pharmacologically acceptable additives among a diluent, a disintegrant and a binder.

5. The candesartan cilexetil-containing preparation according to claim 4, wherein the additive is contained in the range of 500 parts by weight or greater and 10000 parts by weight or less with respect to 100 parts by weight of candesartan cilexetil.

\* \* \* \* \*